United States Patent [19]

Burns

[11] Patent Number: 4,929,742
[45] Date of Patent: May 29, 1990

[54] SILANE MODIFIED POLYSILACYCLOBUTASILAZANES

[75] Inventor: Gary T. Burns, Midland, Mich.

[73] Assignee: Dow Corning Corporation, Midland, Mich.

[21] Appl. No.: 277,080

[22] Filed: Nov. 28, 1988

[51] Int. Cl.$^5$ ............................................. C07F 7/10
[52] U.S. Cl. .................................. 556/406; 528/28; 528/15
[58] Field of Search ................................ 556/406

[56] References Cited

U.S. PATENT DOCUMENTS

| | | | |
|---|---|---|---|
| 2,352,974 | 7/1945 | Rochow | 556/406 X |
| 2,381,002 | 8/1945 | Patnode et al. | 556/406 |
| 2,564,674 | 8/1951 | Cheronis | 556/406 |
| 3,046,291 | 7/1962 | Sommer | 556/406 X |
| 3,178,392 | 4/1965 | Kriver | 556/406 X |
| 3,293,194 | 12/1966 | Lovie et al. | 556/406 X |
| 3,527,781 | 9/1970 | Levin | 556/406 |
| 3,719,696 | 3/1973 | Jonas et al. | 556/406 |
| 3,853,567 | 12/1974 | Verbeek et al. | 556/406 |
| 3,892,583 | 7/1975 | Winter et al. | 556/406 |
| 3,892,713 | 7/1975 | Burkus et al. | 556/406 |
| 4,312,970 | 1/1982 | Gaul | 556/406 |
| 4,328,350 | 5/1982 | Gusehikov et al. | 556/406 |
| 4,340,619 | 7/1982 | Gaul | 556/406 |
| 4,395,460 | 7/1983 | Gaul | 556/406 |
| 4,397,828 | 8/1983 | Seyferth et al. | 556/406 |
| 4,404,153 | 9/1983 | Gaul | 556/406 |
| 4,482,689 | 11/1984 | Haluska | 556/406 |
| 4,535,007 | 8/1985 | Cannady | 556/406 |
| 4,540,803 | 9/1985 | Cannady | 556/406 |
| 4,543,344 | 9/1985 | Cannady | 556/406 |
| 4,675,424 | 6/1987 | King | 556/406 |

FOREIGN PATENT DOCUMENTS 0146802  7/1985  European Pat. Off. ............ 556/406

OTHER PUBLICATIONS

L. W. Breed et al., "Journal of Organic Chemistry", 27, 1114 (1962).
Journal of Polymer Science, A 2 45 (1964).

Primary Examiner—Paul F. Shaver
Attorney, Agent, or Firm—James E. Bittell; Roger E. Gobrogge

[57] ABSTRACT

Polysilacyclobutasilazanes are reacted with chlorosilanes and/or chlorodisilanes and ammonia to provide silane-modified polysilacyclobutasilazanes having silacycles incorporated in the polymer, which silacycles are subsequently used to cross-link the silazanes.

24 Claims, No Drawings

SILANE MODIFIED POLYSILACYCLOBUTASILAZANES

BACKGROUND OF THE INVENTION

This invention relates to the preparation of silane modified polysilacyclobutasilazanes from 1,1-dichloro-1-silacyclobutanes and certain difunctional nucleophiles. These materials are useful as intermediates to form crosslinkable preceramic polymers which, upon pyrolysis, yield ceramic materials.

What is disclosed herein is a novel process to obtain new and novel polymers which contain a strained ring silacycle in the polymer structure.

The process consists of forming silane modified polysilacyclobutasilazanes from polysilacyclobutasilazanes by reacting the polysilacyclobutasilazanes either with chlorosilanes, hereinafter defined, followed by treatment with ammonia or the simultaneous reaction of the ammonia and chlorosilanes with the polysilacyclobutasilazane.

Silazanes in general have been academic curiosities for many years and a variety of such silazanes. including monomers, oligomers, cyclics, low molecular weight and high molecular weight resins and linears have been prepared by a variety of methods, For example, L.W. Breed, et al. in the Journal of Organic Chemistry, 27, 1114 (1962) report the formation of silazanes from the polymerization of sterically hindered silazane oligomers, while in the Journal of Polymer Science, A 2 45 (1964), cyclic trimer and tetramer silazanes are reported to be thermally cracked, using catalysts, to give linear polymers.

In contrast fluids, rubbery polymers, and resins prepared from $CH_3SiCl_3$, $(CH_3)_2SiCl_2$, and excess ammonia have been reported by Kruger, et al. in the Journal of Polymer Science, A 2 3179 (1964).

The patent literature also contains disclosures of the preparation of silazanes. Cheronis in U.S. Pat. No. 2,564,674 discloses the preparation of low molecular weight linear silazane polymers by the reaction of halosilanes with excess ammonia in a solvent solution. Burkus, et al. in U.S. Pat. No. 3,892,713 discloses a similar reaction scheme with the added modification of removing the by-produced solid ammonium halide using ethylene diamine.

Verbeek, et al. in U.S. Pat. No. 3,853,567 and U.S. Pat. No. 3,892,583 disclose that mixtures of $CH_3SiCl_3$ and $(CH_3)_2SiCl_2$ can be treated with ammonia or organoamines to form materials that can be pyrolyzed to yield $SiC/Si_3N_4$ ceramic materials. More recently, Gaul in U.S Pat. No. 4,312,970, issued January 26, 1982, disclosed the preparation of silazane polYmers that were synthesized by reacting various alkyltrichlorosilanes with disilazanes such as $\{(CH_3)_3Si\}_2NH$. In his synthesis, $(CH_3)_3SiCl$ was eliminated as a by-product. These materials can be hyrolyzed at high temperatures to form Si—C—N containing ceramics.

In addition, Gaul, in U.S. Pat. No. 4,404,153, issued July 20, 1982, disclosed preceramic polysilazanes which had been prepared by the reaction of chlorine-containing disilanes and disilazanes.

Cannady, in U.S. Pat. No. 4,543,344 discloses polymers prepared by reacting $HSiCl_3$ and disilazanes and later, Cannady, in U.S. Pat. No. 4,540,803, issued Sept. 10, 1985, described a modification to Gaul's earlier process to include the preparation of a polyhydridomethylsilazane polymer from $HSiCl_3$ and hexamethyldisilazane.

Polymers have been developed and disclosed by Gaul, in U.S. Pat. No. 4,395,460, issued July 26, 1983 and U.S. Pat. No. 4,404,153, issued Sept. 13, 1983; Haluska, in U.S. Pat. No. 4,482,689, issued Nov. 13, 1984; Seyferth, et al. in U.S. Pat. No. 4,397,828, issued Aug. 9, 1983, and U.S. Pat. No. 4,482,669, issued Nov. 13, 1984; Cannady, in U.S. Pat. No. 4,535,007, issued Aug. 13, 1985; Bujalski, in U.S. Pat. application Ser. No. 653,003 filed Sept. 21, 1984; Baney, et al. in U.S. patent application Ser. No. 652,938 filed Sept. 21, 1984 and U.S. patent application Ser. No. 653,939 filed Sept. 21, 1984; and Haluska, in U.S. patent application Ser. Nos. 926,145, filed Nov. 3, 1986 and 926,607, filed Nov. 4, 1986.

Further, in a copending application, Ser. No. 059,718 filed on June 8, 1987 and entitled "Polysilacyclobutasilazanes," the inventor herein, Gary T. Burns, discloses the preparation of yet another new and novel class of silazane polymers: polysilacyclobutasiazanes prepared from 1,1-dichlorosilacyclobutanes and certain nitrogen containing difunctional nucleophiles.

In spite of an intensive search, however, the inventor herein was not able to find any suggestion or teaching in the art regarding the formation of silane-modified polysilacyclobutasilazanes. This invention is based on the utilization of such polysilacyclobutasilazanes as a precursor to still another type of new and novel silazane polymer.

THE INVENTION

This invention relates to a new class of silazane polYmers and a process for their preparation.

More specifically, this invention deals with the preparation of silane-modified polysilacyclobutasilazanes which are prepared by treating the polysilacyclobutasilazanes, hereinafter described, with either chlorosilane(s) and subsequent ammonolysis or with chlorosilane(s) and ammonia essentially simultaneously.

Thus this invention comprises in one regard a process for preparing silane-modified polysilacyclobutasilazanes comprising (I) contacting and reacting in an inert, essentially anhydrous atmosphere, a polymer obtained by contacting and reacting in an inert, essentially anhydrous atmosphere, 1,1-dichloro-1-silacyclobutane having the general formula

$$R_2CR'_2CR''_2CSiCl_2$$

with a difunctional nucleophile selected from the grouP consisting of
(i) ammonia,
(ii) hydrazine, and
(iii) diamines having the general formula HR'''NQNR''''H, wherein R, R', R'', R''', and R'''' are each independently selected from hydrogen, alkyl radicals having from 1 to 4 carbon atoms, aryl groups, and vinyl groups; Q is a divalent hydrocarbon radical; at a temperature less than 75° C for a time sufficient to form polysilacyclobutasilazanes;

(II) separating the polysilacyclobutasilazane from the reaction mass in (I);

(III) contacting and reacting the product from (II) with a chlorosilane or a mixture of chlorosilanes selected from chlorosilanes and chlorodisilanes having the general formula (i) $(R^v)_m SiCl_{4-m}$ and (ii) $\{Si(R^v)_t Cl_{3-t}\}_2$ wherein each $R^v$ is independently selected from hydrogen, alkyl radicals having from 1 to 4 carbon atoms, aryl groups, and vinyl groups; m is 0, 1, or 2; and t is 0 to 2;

(IV) contacting and reacting the product from (III) with dry gaseous ammonia; and (V) recovering the product from (IV).

In another regard, this invention comprises a process for preparing silane-modified polysilacyclobutasilazanes comprising (I) contacting and reacting in an inert, essentially anhydrous atmosphere, a polymer obtained by contacting and reacting in an inert, essentially anhydrous atmosphere, 1,1-dichloro-1-silacyclobutane having the general formula

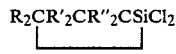

with a difunctional nucleophile selected from the group consisting of (i) ammonia, (ii) hydrazine, and (iii) diamines having the general formula $HR''''NQNR''''H$, wherein R, R', R'', R''', and R'''' are each independently selected from hydrogen, alkyl radicals having 1 to 4 carbon atoms, aryl groups, and vinyl groups; Q is a divalent hydrocarbon radical; at a temperature less than 75° C, for a time sufficient to form polysilacyclobutasilazane;

(II) separating the polysilacyclobutasilazane from the reaction mass in (I);

(III) simultaneously contacting and reacting the product from (II) with either (i)(a) a chlorosilane or a mixture of chlorosilanes selected from chlorosilanes having the general formula $(R^v)_m SiCl_{4-m}$ or (b) a chlorodisilane or a mixture of chlorodisilanes having the general formula $\{Si(R^v)_t Cl_{3-t}\}_2$ or mixtures of (a) and (b) wherein each $R^v$ is independently selected from hydrogen, alkyl radicals having from 1 to 4 carbon atoms, aryl groups, and vinyl groups; m is 0, 1, or 2; t is 0 to 2; and (ii) ammonia; and (IV) recovering the product from (III).

This invention also deals with new compositions of matter which are the silane-modified polysilacyclobutasilazanes prepared by the various processes of the invention described herein.

Further, this invention also deals with crosslinked silane-modified polysilacyclobutasilazanes and a process for crosslinking such polymers.

Still further, this invention also relates to a process of converting the inventive compositions to ceramic materials and the ceramic compositions prepared thereby.

Turning now to the inventive process, those skilled in the art will appreciate from the following that the process deals with the silane-modification of polysilacyclobutasilazanes by two alternative methods.

The first method relates to the silane modification of a polysilacyclobutasilazane with subsequent ammonolysis and the second method deals with the co-reaction of the polysilacyclobutasilazane chlorosilane(s), and ammonia to give the silane-modified polymers.

The polysilacyclobutasilazanes useful in this invention are those taught by Burns in the copending application Ser. No. 059,718 entitled, "Polysilacyclobutasilazanes," filed on June 8, 1987, which is hereby incorporated by reference. Burns teaches in that invention the reaction of 1,1-dichlorosilacyclobutanes with certain nitrogen-containing difunctional nucleophiles. Thus, Burns teaches, for example, the reaction

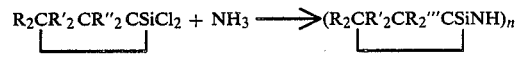

where n is greater than two.

Further, Burns teaches the use of difunctional amines and hydrazine as reactive substitutes for $NH_3$ to form respectively

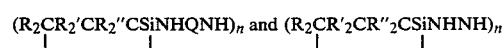

wherein n is at least 2.

These reactions are carried out at temperatures of 75° C or lower. Preferred reaction temperatures are below 25° C and most preferred in the range of −20° C to −30° C.

The present invention, therefore, deals with the modification of these polymers using chlorosilanes and ammonia where in one case, the silanes are reacted with the polymers and then subsequently with ammonia and, in an alternate case, the coreaction of a chlorosilane and ammonia with the polymers. The reactions can be carried out in an inert, essentially anhydrous atmosphere. What is meant herein by "inert" is that the reaction should be run in the absence of air or any gas which is reactive with any of the reactants.

"Essentially anhydrous" for purposes of this invention means that the entire process should be carried out wherein precautions are taken to prevent the introduction of water into the process of the instant invention at any stage of the process, as water lends oxygen to the reactants resulting in inferior properties in the ceramic products prepared from these silane-modified polymers.

Further, water tends to cause hydrolysis of the reactants, especially the chlorosilanes and chlorodisilanes used in this process.

Water should, therefore, be avoided, it being understood by those skilled in the art that small amounts of moisture will probably be present even with precautions to prevent incorporation of the same.

"Contacting," for purposes of this invention, means any convenient method by which the materials of the reaction can be brought together. Any manner of bringing the reactants together is acceptable herein, as long as the reactants can contact and react. Preferred for this inventive process is simple mixing whereby, in the case of the formation of the polysilacyclobutasilazane, the difunctional nucleophile is added to the silacyclobutane in a reaction vessel. The silane-modified polymer is handled generally by adding the silane to the polymer in solvent, either bubbling ammonia through the polymer solution after the initial silane modification or simultaneously therewith.

The addition of the chlorosilane or the simultaneous addition of the chlorosilane or chlorodisilanes and the ammonia to polysilacyclobutasilazane should be conducted at relatively low temperatures The reaction temperature is somewhat solvent dependent. For polar solvents such as methylene chloride, the preferred temperature range is −50° to 25° C. For less polar solvents such as toluene, the preferred temperature range is about 0° to 60° C. Many methods are known in the art to maintain the reaction mass at these low temperatures and such procedures are useful herein.

By "simultaneous" the inventor herein means that the chlorosilane or chlorodisilanes and the ammonia can be added to polysilacyclobutasilazane at the same time. As indicated above, the chlorosilane or chlorodisilane addition can also be started and followed sometime later by the ammonia treatment.

"Reacting" for purposes of this invention means in step (I), the reaction of the 1,1-dichloro-1-silacyclobutane with the nitrogen containing difunctional nucleophile to form the intended polymers, which polymers are those set forth and described in Burns, U.S. patent application Ser. No. 059,718 filed June 8, 1987. Such polymers are included herein by reference as those polymers useful for the silane-modification of the instant invention "Reacting" for purposes of this invention means in Step (III), the reaction of the chlorine(s) of the chlorosilanes or disilanes and the ammonia with the polymer formed in Step (1) to form a new. silane-modified polymer of the invention.

"Sufficient time" means an adequate amount of time for the various reactions to take place in the process of this invention Generally, a time of about thirty minutes of contact, after the addition of the reactants is complete, is sufficient. Enough time should be allowed to form the highest yield possible. Thus it is preferred for purposes of this invention to allow the reaction in Step (I) to proceed for at least four hours and it is generally Preferred to allow the reaction to run at least seven hours, but not more than twenty four hours. In Step (III), the preferred amount of time is at least thirty minutes after the reactants have been contacted and it is more preferred to run the reaction of Step (III) for at least two hours after the reactants have been contacted.

In Step (I), the Polysilacyclobutasilazane is separated from the reaction mass by any known convenient means such as filtering and the like, it being understood that undue exposure of the product to the air should be avoided.

Solvents useful in this process are any of those organic solvents that are not reactive with the dichlorosilacyclobutane, difunctional nucleophiles, or chlorosilanes, and which solubilize such reactants. Preferred polar solvents for this process are chlorinated hydrocarbons; most preferred is methylene chloride. Non-polar solvents may also be employed in this invention; toluene is the preferred non-polar solvent.

Thus, in order to prepare polysilacyclobutasilazanes one generally places the dichlorosilacyclobutane in a reaction vessel, which has been prepared bY excluding air and moisture, and blanketing the silacyclobutane with, for example, dry argon, said reaction vessel being equipped with at least a thermal indicator means, stirrer means, appropriate cooling and heating means, and devices for the addition of any additional reactants. The reaction vessel and its contents are cooled to the desired temperature and the difunctional nucleophile is added dropwise to the silacyclobutane with stirring, all the time maintaining the inert blanket of gas over the reaction medium. After this addition is complete, the reaction mass is allowed to stir either at reaction temperature, or at a higher temperature (up to about 75° C) for a time sufficient to form the desired polymer. The polymer is then separated from the reaction mass. At this point, the solvent can be left in the separated polymer or it can be removed. Generally, the polymer is stored without solvent, but in the invention, it is best that the solvent should remain and the polymer is contacted in the solvent form when reacted with the chlorosilane, chlorodisilane, or a mixture of chlorosilanes and/or chlorodisilanes having the general formulae described infra.

The reacting of the chlorosilane can be accomplished with or without the simultaneous treatment of the polymer with ammonia. Thus, the chlorosilane(s) and/or chlorodisilane(s) and the ammonia can be reacted essentially simultaneously or the chlorosilane(s) and/or chlorodisilane(s) can be first reacted with the polymer and then with the ammonia. The purpose of the ammonia treatment is to reduce the chlorine content of the resulting chlorosilane(s)/polysilacyclobutasilazane reaction product.

After the treatment as described above, the resulting product is separated from the reaction mass, using filtration or some other similar means.

This invention also deals with new and novel compositions of matter which are the silane-modified polysilacyclobutasilazanes wherein the resulting silazane contains silacycle structures. These compositions are based on the reaction of polysilacyclobutasilazanes described by Burns, U.S. patent application Ser. No. 059,718 filed on June 8, 1987 with chlorosilanes and/or chlorodisilanes and ammonia wherein the chlorosilanes and/or chlorodisilanes or mixtures thereof are selected from chlorosilanes and chlorodisilanes having the general formula (i) $(R^v)_m SiCl_{4-m}$ and
(ii) $\equiv Si(R^v)_t Cl_{3-t}\}_2$ wherein each $R^v$ is defined above; m is 0, 1, or 2; and t is 0 to 2; until a chlorosilyl end-blocked polysilacyclobutasilazane is obtained; (IV) contacting and reacting the product from (III) with dry gaseous ammonia to reduce the amount of chlorine in the product (III); and (V) recovering the product from (IV).

For purposes of this invention, examples of the chlorosilanes that are useful herein are $HSiCl_3$, $CH_3SiCl_3$, $SiCl_4$, $(CH_3)_2SiCl_2$, and mixtures thereof. Examples of chlorodisilanes that are useful herein include 1,2-dichloro-1,1,2,2-tetramethyldisilane, 1,1,2-trichloro-1,2,2-trimethyl-disilane and 1,1,2, 2-tetrachloro-1,2-dimethyldisilane, and mixtures thereof. For the disilanes of formula $\{Si(R^v)_t Cl_{3-t}\}_2$, t is between 0 and 2 inclusive. As one skilled in the art will realize, t more specifically can be 0, 0.5, 1.0, 1.5, or 2.

Because the reaction of the chlorosilanes or chlorodisilanes with the polysilacyclobutasilazane provides a polymer containing residual -SiCl groups and since chlorine is detrimental to the final product relative to its intended end use, the silane-modified polysilacyclobutasilazane containing residual chlorine on silicon atoms is treated with ammonia to reduce the amount of such chlorine. As can be noted from the examples, this step can easily be effected by bubbling ammonia through the reaction mixture for several hours. Generally two hours is sufficient.

In an alternate method of preparation, the silane-modified polymer of this invention can be further modified by the incorporation of certain cyclic silazanes during the formation of the silane-modified polymers. The cyclic silazanes are mixed with the chlorosilanes or chlorodisilanes and the polysilacyclobutasilazane and co-reacted thereby. The cyclic silazanes useful in this invention are those having the general formulae
 (i) $(CH_3R^{vi}SiNH)_x$ and
 (ii) $(C_6H_5R^{vii}SiNH)_x$
wherein each $R^{vi}$ and $R^{vii}$ is independentlY selected from the group consisting of hydrogen, vinyl, aryl, and alkyl radicals containing 1 to 4 carbon atoms and x has a value of 3, 4, 5, or 6. Preferred for this invention are those cyclic silazanes wherein x has a value of 3 or 4 and $R^{vi}$ and $R^{vii}$ are methyl, vinyl, or phenyl. Most preferred are those cyclics wherein x has a value of 4 and $R^{vi}$ and $R^{vi}$i are methyl. Mixtures of cyclic silazanes can be used. By "mixture" it is meant for purposes of this invention that the cyclics can be mixtures wherein x has the value of 3 or 4, or x has a value of 3. 4, and 5, etc. Generally, the cyclic silazanes are used in such mixtures wherein the cyclic tetramer predominates, that is, the cyclic tetramer is present in the mixture in more than fifty weight percent. "Mixtures" can also mean that, for example, cyclic tetramers having different substituents on silicon can be used. For example, $\{(CH_3)_2SiNH\}_4$ and $\{CH_3(CH_232 CH)SiNH\}_4$ can be used together to give mixed polymers.

These silane-modified polysilacyclobutasilazanes range from viscous oils to semi-soft solids in physical appearance.

These polymers, prepared by the inventive process herein, are believed to self-crosslink through the thermally initiated ring opening of the silacycles incorporated in the silazane polymers. The modified polysilacyclobutasilazane prepared by the sequential contacting process can be crosslinked by heating the polymer in the presence of dry air to a temperature of 180° to 280° C. The modified polysilacyclobutasilazane prepared by the simultaneous contacting process can be crosslinked by heating the polymer in the absence of air to a temperature of 140° to 230° C. This crosslinking can also be initiated by catalysts Catalysts considered useful in this regard are, for example, metal hydrides, such as sodium, potassium, or lithium hydrides; metal alkoxides such as sodium, potassium, or lithium methoxides; me!al amides such as, for example, lithium diethylamide; rhodium catalysts such as Wilkinson's catalyst; and platinum catalysts such as chloroplatinic acid.

With the exception of the hydrazine based, silane-modified polysilacyclobutasilazane, this invention also contemplates the use of these non-oxidatively cross-linked polYmers of this invention in the preparation of ceramic materials by the pyrolysis of such crosslinked polymers at elevated temperatures, that is, in excess of 700° C. The pyrolysis may be carried out under an inert atmosphere or under vacuum. Ceramic materials can be prepared using these crosslinked polymers with char yields ranging from 60 to 80 percent with low oxygen contents ranging from 1 to 4 percent when fired at 1200° C in argon.

All of the ceramics prepared thereby have excellent oxidative stability

These polymers are susceptible of being shaped by subjecting them to slight or moderate crosslinking and then shaping and subsequently finishing the crosslinking to set the shape. The shaped polymers hold their shape upon firing and exhibit low shrinkage and weight loss at the elevated temperatures. Likewise, these materials are extrudable.

Now so that those skilled in the art can better understand and appreciate the invention, the following examples are given. These examples are for purposes of illustration only and are not to be regarded as limitations on the scope of the invention as presented herein.

All of the polymers were characterized by a combination of $^1H$ NMR, infrared analysis, elemental analysis, gel phase chromatography (GPC) thermogravimetric, and thermomechanical analysis (TGA and TMA respectively).

$^1H$ NMR spectra were obtained on a Varian EM-390, 90 MHz instrument and are reported in delta values; infrared spectra were obtained on a Nicolet DX5 Spectrophotometer under a nitrogen atmosphere. TMA was done on a DuPont 940 thermomechanical analyzer. TGA was done on an Omnitherm TGA interfaced with a Omnitherm 2066 computer. GPC was carried out on a DuPont Instruments GPC equipped with a Spectra Physics SP4100 integrator and a DuPont refractive index detector. The GPC molecular weights are based upon a calibration curve derived from fractionated silazane polymers prepared by the method of Gaul in U.S. Pat. No. 4,340,619 using polystyrene standards.

Elemental analysis of carbon, hydrogen, and nitrogen was done by a method of catalytic oxidation of the sample. Carbon and hydrogen are measured as carbon dioxide and water. Nitrogen is measured in the elemental form. Such analyses were carried out essentially by the methods set forth in Niederl and Niederl, "Micromethods of Quantitative Organic Analysis", 2d ed., 1942, John Wiley and Sons.

Silicon was determined by a method of atomic absorption spectrometry/fusion techniques. Silicon containing materials and mixtures are converted to a soluble form of silicon and the soluble silicon is quantitatively determined in the percent range as total silicon by atomic absorption spectrometry. Samples are weighed and fused by any generally accepted techniques. The fusionate is solubilized, diluted to a known volume with distilled water, and analyzed in a spectrophotometer.

Total chloride was determined by a method of sodium peroxide decomposition and the decomposition product was titrated using silver nitrate.

Curing temperatures were determined by using differential scanning calorimetry analysis of the polymer.

A silane-modified polysilacyclobutasilazane was prepared in the following manner:

A solution of 400 (2.84 moles) of

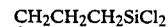
$$\overline{CH_2CH_2CH_2SiCl_2}$$

in 2.5 liters of methylene chloride was treated by bubbling ammonia gas through the solution while the temperature of the solution was maintained between $-20°$ and $-40°$ C for seven hours. At the end of seven hours, the reaction mass was warmed to room temperature, filtered through a medium glass frit and concentrated by rotary evaporation; the filtration, being rapid, was not done in an inert gas. The yield of the polysilacyclobutasilazane was 219 g. A portion of these materials in methylene chloride was placed in a 3-necked round-bottomed glass reaction vessel fitted with a mechanical stirrer, Dewar condenser, a gas outlet tube, and a gas inlet tube. The reaction mass was cooled to $-15°$ to $-20°$ C and a chlorosilane was added in one portion and the solution was warmed to about 5° C over a period of 1 hour with stirring. The reaction mass was then cooled to −20° C and ammonia gas was bubbled through the reaction mass for several hours. After warming to room temperature, the reaction mass was filtered and the filtrate concentrated by removal of the solvent at reduced pressure.

Under the above conditions, the following silanes were used:

EXAMPLE 1

Using 9.18 g (0.108 equiv.) of polysilacyclobutasilazane and 3.758 g (0.028 mole) of HSiCl₃ gave 8.30 g of a viscous oil for a 77.8% yield. The product had the following analysis: ¹H NMR (CDCl₃): 1.37 (m), 1.70 (m), 4.80 (broad s). The ratio of

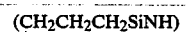

to —SiH was 33 to 1.0. Infrared (film) showed 3378 (m), 2968 (m), 2923 (m), 2869 (w), 2147 (m), 1450 (w), 1409 (m), 1393 (m), 1196 (s), 1174 (s), 1123 (s), 1034 (m), 952 (s), 691 (m). Elemental analysis gave 38.1% C, 9.02% H, 17.1% N, and 35.5% Si.

EXAMPLE 2

Using 24.085 g (0.2834 equiv.) of the polysilacyclobutasilazane and 20.67 g (0.1525 mole) of HSiCl₃ gave 25.17 g of a viscous oil for a 78.8% yield. ¹H NMR (CDCl₃): 1.36 (m), 1.64 (m), 4.86 (m, Si—H). The ratio of

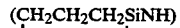

to —SiH was 12.8 to 1.0. IR film: 3377 (s), , 2922 (s), 2868 (m). 2147 (s), 1450 (w), 1409 (w), 1393 (m). 1196 (s), 1174 (s). 1123 (s), 952 (s), 691 (m). GPC molecular weight: Mw=361, Z avg. =636, Mn =214, Z 1 avg. =956, Mw/Mn =1.69. VPO Molecular Weight=670. Elemental analysis gave 34.8% C, 8.14% H, 17.0% N, and 37 8% Si.

EXAMPLE 3

Using 10.40 g (0.1202 equiv.) of the polysilacyclobutasilazane and 7.134 g (0 042 mole) of SiCl4 gave 905 g of a soft solid for a 70.5% yield. ¹H NMR (CDCl₃): (m), 1.61 (m). IR film: 3378 (s), 2959 (s), 2923 (s), 2869 (m), 1447 (w), 1409 (m), 1393 (m), 1179 (s), 1122 (s), 941 (s). 687 (m). GPC Molecular Weight; Mw=1558, Z avg.=6320, Mn=303, Z+1 avg.=11207, Mw/Mn =5.14. Elemental analysis gave 23.2% C, 7.15H, 3.38% N, and 22.9% Si.

EXAMPLE 4

Using 17.20 % (0.202 equiv.) of the polysilacyclobutasilazane and 18.25 % (0.107 mole) of SiCl4 gave 11.08 g of a soft solid for a 47% yield. ¹H NMR (CDCl₃): 0.63 to 2.13 (m). IR film: 3381 (m, NH), 2959 (m), 2868 (m), 1447 (w), 1409 (w), 1391 (w), 1202 (s), 1180 (s), 1124 (s), 941 (s), 689 (m). Elemental analysis gave 35.2% C, 7.72% H, 17.2% N, and 34.5% Si.

EXAMPLE 5

Using 17.59 % (0.207 equiv.) of the polYsilacyclobutasilazane and 22.95 % (0.154 mole) of CH₃SiCl₃ gave 19.87 % of a soft solid for a 71.8% yield. ¹H NMR (CDCl₃): −0.17 to 0.33 (broad m), 0.53 to 2.03 (broad m). The CH₃Si to

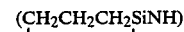

ratio was 4.0 to 1. IR film: 3381 (m), 2959 (s), 2927 (s), 2868 (m), 1447 (w), 1406 (w), 1391 (w), 1258 (s), 1180 (s), 1032 (w), 955 (s), 752 (m), 694 (m). GPC Molecular Weight: Mw=1057, Z avg.=7566, Mn=238, Z+1 avg.=12820, Mw/Mn=4.43. Elemental analysis gave 32.7% C, 7.40% H, 6.46% N, and 34.5% Si.

EXAMPLE 6

Using 17.07 g (0.201 equiv.) of the polysilacyclobutasilazane and 14.0 g of methylchlorodisilanes (consisting of 10.76% 1,2-dichloro-1,1,2,2-tetramethyldisilane, 30.16% 1,1,2-trichloro-1,2,2trimethyldisilane, and 57.62%, 1,1,2,2-tetrachloro-1,2-dimethyldisilane) gave 21.0 g of a viscous, tacky oil in 85.7% yield. ¹H NMR (CDCl₃): 0.15 (broad s), 0.72 to 2.02 (m). The ratio of

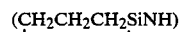

to —SiCH₃ was 2.68 to 1.IR film: 3381 (m), 2959 (s). 2932 (s), 2868 (m), 2783 (w), 1447 (w), 1406 (m), 1391 (m) 1250 (m)3, 1167 (s), 1124 (s), 1032 (m). 934 (s), 758 (m), 689 (m). GPC Molecular Weight: Mw =916, Z avg. =950, Mn =878, Z +1 avg. =979, Mw/Mn =1.04. Elemental analysis showed 36.6% C, 8.68% H, 14.0% N, and 3.3% Si.

EXAMPLE 7

Ammonolysis of polysilacyclobutasilazane using HSiCl₃ and octamethylcyclotetrasilazane.

A 100 mL 3-necked, round-bottomed glass flask equipped with a Dewar Condenser with a gas outlet port, a mechanical stirrer, and a gas inlet tube was charged with 4.173 g (0.0491 mole) of polysilacyclobutasilazane prepared by bubbling ammonia gas through a solution of 400 g (2.84 moles) of

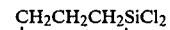

in 2.5 liters of methylene chloride, while the temperature of the solution was maintained between −20° and −40° C for seven hours. At the end of seven hours, the reaction mass was warmed to room temperature, filtered through a medium glass frit, and concentrated by rotary evaporation, the filtration, being rapid, was not done in an inert gas. The yield of the polymer was 219 g. To this polymer was added 3.617 % (0.0495 mole) of octamethylcyclotetrasilazane and 70 mL of methylene chloride. The solution was cooled to −5° C and 7.247 g (0.053 mole) of HSiCl₃ was added in one portion. The reaction was allowed to warm to 5° C over a 60 minute period. After recooling to −30° C, ammonia was rapidly bubbled through the solution for 3 hours. The reaction was then warmed to room temperature, filtered through Celite, and the filtrate was concentrated in vacuo to afford 4.871 g ⓒf a viscous oil for a yield of 45.3%. ¹H NMR (CDCl₃): 0.19 (s), 1.36 (m), 1.59 (m), 4.77 (broad s). The (CH₃)₂Si to (CH₂CH₂CH₂SiNH) to —SiH ratio was 6.8 to 10.4 to 1.0. IR film: 3386 (s), 2959 (s), 2139 (s), 1409 (w), 1253 (s), 1179 (s), 941 (s), 835 (s), 786 (s), 695 (m). Elemental analysis gave 27.7% C, 7.28% H, 18.6% N, and 40.3% Si.

EXAMPLE 8

The material of example 2, designated (A), was compared against prior art material, designated (B), which was prepared by ammonolysis of hexamethylcyclotrisilazane and HSiCl₃. A 250 ml, 3-necked, round-bottomed glass flask fitted with a mechanical stirrer, a Dewar Condenser with a gas outlet, and a gas inlet tube was charged with 20.70 g (0.0945 mole) of hexamethylcyclotrisilazane and 200 mL of methylene chloride. The solution was cooled to −20° C and 20.67 g (0.153 mole) of HSiCl₃ was added in one portion. The solution was warmed to 10° C over a 45 minute period, recooled to −20° C, and ammonia was rapidly bubbled through the solution for 2 hours. After warming to room temperature, the solution was filtered through Celite and concentrated at reduced pressure to give 19.3 % of product as a clear, viscous oil (67.6% yield). $^1$H NMR (CDCl₃): 0.13 (s), 0.52 to 1.25 (broad m, N—H), 4.55 to 5.19 (broad m). The CH₃Si to NH to —SiH ratio was 10 to Z.86 to 1.0.

Each of the samples (A) and (B) was heated in a glass vial immersed in an oil bath. Sample (A) was a 4.565 g sample and (B) was a 4.066 g sample. At 210°–215° C sample (A) gelled. The samples were heated to 255° C and then cooled to room temperature. Sample (B) remained a low viscosity liquid soluble in methylene chloride while sample (A), upon gelling, was a brittle, insoluble solid.

EXAMPLE 9

Several of the polymers prepared herein were checked to determine the thermal point at which the silacycle ring was opened and crosslinking was initiated.

Thus, for this test, a side-arm flask, fitted with a thermometer and a stirring bar, was charged with 1 to 3 g of the polymer. The flask was evacuated and backfilled with either argon or dry air. The flask was heated and the gel temperature recorded. Differential scanning calorimetry (DSC) using a helium atmosphere was used to also determine the onset of crosslinking. The results are found in the following Table I.

TABLE I
OBSERVED AND MEASURED POLYMERIZATION ONSET TEMPERATURES

| Example | Atmosphere | Temperature, °C. Observed | Measured (DSC) |
|---|---|---|---|
| 1 | argon | 180 | 173 |
| 2 | dry air | 220 | — |
| 2 | argon | 220 | 209 |
| 3 | argon | 140 | 150 |
| 4 | argon | 220 | 200 |
| 5 | — | — | 188 |
| 6 | argon | 220 | 182 |
| 7 | argon | 230 | 214 |

EXAMPLE 10

Crosslinked polymers of this invention were subjected to pyrolysis to convert them to ceramic materials by loading portions of the polymers into mullite boats and transferring the boats under argon to a four-inch, three-zone Lindberg tube furnace. The samples were pyrolyzed din an inert atmosphere to 1200° C at 5° C/min, held at 1200° C for 30–40 minutes, and then allowed to cool to room temperature over a 14–18 hour interval. The results are as shown in Table II, wherein results are also shown for samples pyrolyzed in air.

TABLE II
CERAMIC CHAR YIELDS

| Example | Crosslink Atmosphere | TGA Char yield[1] | Bulk Char yield[2] |
|---|---|---|---|
| 1 | argon | 67 | 68.1 |
| 1 | dry air | — | 78.6 |
| 2 | — | 77 | 80.1 |
| 4 | — | 71 | 72.8 |
| 5 | — | 58.5 | 65.9 |
| 6 | — | 74.2 | 68.2 |
| 7 | — | 66 | 68.8 |

[1]Helium or nitrogen atmospherel
[2]Argon atmospherel

The ceramics were analyzed and the results can be found in Table III.

TABLE III
ELEMENTAL ANALYSIS OF THE CERAMIC CHAR

| | Weight % Fired 1200° C./argon | | | | Weight % Fired 1200° C./air | | | |
|---|---|---|---|---|---|---|---|---|
| Example | C | N | Si | O | C | N | Si | O |
| 1 | 30.4 | 19.6 | 46.4 | 2.93 | | | | 3.29 |
| 2 | 26.4 | 22.4 | 48.3 | 1.86 | | | | 2.16 |
| 4 | 24.7 | 23.3 | 46.9 | 3.06 | | | | 3.38 |
| 5 | 20.6 | 22.5 | 49.7 | 2.15 | 19.1 | 2.35 | 49.5 | 3.56 |
| 6 | 25.8 | 16.4 | 49.3 | 2.21 | | | | 3.56 |
| 7 | 19.1 | 24.0 | 52.3 | 1.80 | | | | 1.22 |

EXAMPLE 11

The ceramic samples were loaded into mullite boats and transferred to a four-inch, three-zoned Lindberg tube furnace. The samples were heated in a dry purged air atmosphere from room temperature to 1200° C at 5° C/min and held at 1200° C for 12 hours. The oxygen content of the ceramics was measured by well-known LECO analysis. The results are shown in Table IV.

TABLE IV
OXIDATION WEIGHT RETENTION

| Example | % Retention | Ceramic Density |
|---|---|---|
| 1 | 98.1 | 2.217 |
| 2 | 96.7 | 2.195 |
| 4 | 98.8 | 2.187 |
| 5 | 99.4 | 2.353 |
| 6 | 98.5 | 2.244 |
| 7 | 98.3 | 2.217 |

EXAMPLE 12

A mixture of

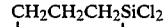

$CH_2CH_2CH_2SiCl_2$ (141 g, 1.0 moles) and dephenyldichlorsilane (63 g, 0.25 moles) in 3 liter toluene were reacted by bubbling ammonia (diluted to about 50 volume percent with argon) through the mixture. During the reaction the temperature was kept below 25° C; the ammonia addition was stopped when the temperature fell to 20° C. The reaction mixture was filtered and added to a reaction flask under argon. Methyltrichlorsilane (90 g, 0.6 moles) was added over a 15 minute period. This reaction mixture was heated to 60° C for 12 hours. After cooling to about 20° C, ammonia was bubbled through the mixture. The temperature rose to about 25° C. The ammonia treatment was continued until the temperature fell to about 20° C. The reaction mixture was filtered and then concentrated to about one liter. This concentrate was refiltered and then stripped at 180 to 190° C under vacuum for 2 hours. The polymer yield was 78.7% (136.5 g).

I claim:

1. A process for preparing modified polysilacyclobutasilazanes comprising:
   (A) contacting and reacting in an inert, essentially anhydrous atmosphere, a polysilacyclobutasilazane polymer with a compound or mixture of compounds selected from the group consisting of
   (i) chlorosilanes having the general formula $(R^v)_m SiCl_{4-m}$ and (ii) chlorodisilanes having the general formula ${Si(R^v)_t Cl_{3-t}}_2$ where, in the general formulae for chlorosilanes and chlorodisilanes, each $R^v$ is independently selected from the group consisting of hydrogen, alkyl radicals having 1 to 4 carbon atoms, aryl radicals, and the vinyl radical; m is 0, 1, or 2; and t is 0 to 2;
   at a temperature less than 100° C for a time sufficient to form a partially modified polysilacyclobutasilazane polymer,
   (B) contacting and reacting the partially modified polysilacyclobutasilazane polymer with dry ammonia, and
   (C) recovering modified polysilacyclobutasilazane polymer.

2. A process as claimed in claim 1 wherein the polysilacyclobutasilazane polymer is prepared by contacting and reacting, at a temperature less than 75° C, in an inert, essentially anhydrous atmosphere, a silacyclobutane having the general formula $R_2CR'_2CR''_2CSiCl_2$
   |_____| with a difunctional nucleophile selected from the group consisting of
   (i) ammonia,
   (ii) hydrazine, and
   (iii) diamines having the general formula $HR'''NQNR''''H$, where, in the general formulae, each R, R', R'', R''', and R'''' is independently selected from the group consisting of hydrogen, alkyl radicals having 1 to 4 carbon atoms, aryl radicals, and the vinyl radical and Q is a divalent hydrocarbon radical, for a time sufficient to form polysilacyclobutasilazane.

3. A process as claimed in claim 1 wherein the contacting and reacting of polysilacyclobutasilazane polymer with a compound or mixture of compounds is carried out in a polar solvent at a temperature in the range of minus 50° to 25° C.

4. A process as claimed in claim 1 wherein the contacting and reacting of polysilacyclobutasilazane polymer with a compound or mixture of compounds is carried out in a non-polar solvent at a temperature in the range of 0° to 60° C.

5. A modified polysilacyclobutasilazane polymer prepared by the process of claim 1.

6. A modified polysilacyclobutasilazane polymer prepared by the process of claim 2 wherein the polysilacyclobutasilazane polymer is prepared by contacting and reacting 1,1-dichloro-1silacyclobutane with ammonia.

7. A modified polysilacyclobutasilazane polymer prepared by the process of claim 2 wherein the polysilacyclobutasilazane polymer is prepared by contacting and reacting 1,1-dichloro-1silacyclobutane with hydrazine.

8. A modified polysilacyclobutasilazane polymer prepared by the process of claim 2 wherein the polysilacyclobutasilazane polymer is prepared by contacting and reacting 1,1-dichloro-1silacyclobutane with $H_2N(CH_2)_2NH_2$.

9. A modified polysilacyclobutasilazane polymer prepared by the process of claim 1 wherein the compound contacted and reacted with the polysilacyclobutasilazane polymer is $HSiCl_3$.

10. A modified polysilacyclobutasilazane polymer prepared by the process of claim 1 wherein the compound contacted and reacted with the polysilacyclobutasilazane polymer is $CH_3SiCl_3$.

11. A modified polysilacyclobutasilazane polymer prepared by the process of claim 1 wherein the compound contacted and reacted with the polysilacyclobutasilazane polymer is $(CH_3)_2SiCl_2$.

12. A modified polysilacyclobutasilazane polymer prepared by the process of claim 1 wherein the compound contacted and reacted with the polysilacyclobutasilazane polymer is $SiCl_4$.

13. A modified polysilacyclobutasilazane polymer prepared by the process of claim 1 wherein a mixture of compounds is contacted and reacted with the polysilacyclobutasilazane polymer.

14. A process for preparing modified polysilacyclobutasilazanes comprising:
    (A) simultaneously contacting and reacting in an inert, essentially anhydrous atmosphere, a polysilacyclobutasilazane polymer with dry ammonia and a compound or mixture of compounds selected from the group consisting of
    (i) chlorosilanes having the general formula $(R^v)_m SiCl_{4-m}$ and (ii) chlorodisilanes having the general formula ${Si(R^v)_t Cl_{3-t}}_2$ where, in the general formulae for chlorosilanes and chlorodisilanes, each $R^v$ is independently selected from the group consisting of hydrogen, alkyl radicals having 1 to 4 carbon atoms, aryl radicals, and the vinyl radical; m is 0, 1, or 2; and t is 0 to 2;
    at a temperature less than 75° C for a time sufficient to form a modified polysilacyclobutasilazane polymer, and
    (B) recovering modified polysilacyclobutasilazane polymer.

15. A modified polysilacyclobutasilazane polymer prepared by the process of claim 14.

16. A modified polysilacyclobutasilazane polymer prepared by the process of claim 14 wherein the compound contacted and reacted with the polysilacyclobutasilazane polymer is $HSiCl_3$.

17. A modified polysilacyclobutasilazane polymer prepared by the process of claim 14 wherein the compound contacted and reacted with the polysilacyclobutasilazane polymer is $CH_3SiCl_3$.

18. A modified polysilacyclobutasilazane polymer prepared by the process of claim 14 wherein the compound contacted and reacted with the polysilacyclobutasilazane polymer is $(CH_3)_2SiCl_2$.

19. A modified polysilacyclobutasilazane polymer prepared by the process of claim 14 wherein the compound contacted and reacted with the polysilacyclobutasilazane polymer is $SiCl_4$.

20. A modified polysilacyclobutasilazane polymer prepared by the process of claim 14 wherein a mixture of compounds is contacted and reacted with the polysilacyclobutasilazane polymer.

21. A process for preparing modified polysilacyclobutasilazanes comprising:
(A) contacting and reacting in an inert, essentially anhydrous atmosphere, a mixture of
  (1) polysilacyclobutasilazane polymer and
  (2) a cyclic silazane or mixture of cyclic silazanes selected from the group consisting of $\{CH_3(R^{vi})SiNH\}_x$ and $\{C_6H_5R^{vii})SiNH\}_x$ wherein each $R^{vi}$ and $R^{vii}$ is independently selected from the group consisting of hydrogen, alkyl radicals containing 1 to 4 carbon atoms, aryl radicals, and the vinyl radical and x has a value of 3, 4, 5, or 6;
with a compound or mixture of compounds selected from the group consisting of
(i) chlorosilanes having the general formula $(R^v)_mSiCl_{4-m}$ and (ii) chlorodisilanes having the general formula $\{Si(R^v)_tCl_{3-t}\}_2$ where, in the general formulae for chlorosilanes and chlorodisilanes, each $R^v$ is independently selected from the group consisting of hydrogen, alkyl radicals having 1 to 4 carbon atoms, aryl radicals, and the vinyl radical; m is 0, 1, or 2; and t is 0 to 2;
at a temperature less than 100° C for a time sufficient to form a partially modified polysilacyclobutasilazane polymer,
(B) contacting and reacting the partially modified polysilacyclobutasilazane polymer with dry ammonia, and
(C) recovering modified polysilacyclobutasilazane polymer.

22. A modified polysilacyclobutasilazane polymer prepared by the process of claim 21.

23. A process for preparing modified polysilacyclobutasilazanes comprising:
(A) contacting and reacting in an inert, essentially anhydrous atmosphere, a polysilacyclobutasilazane polymer with a mixture consisting essentially of 1,2-dichloro-1,1,2,2-tetramethyldisilane, 1,1,2-trichloro-1,2,2-trimethyldisilane, and 1,1,2,2-tetrachloro-1,2-dimethyldisilane to form a partially modified polysilacyclobutasilazane polymer,
(B) contacting and reacting the partially modified polysilacyclobutasilazane polymer with dry ammonia, and
(C) recovering modified polysilacyclobutasilazane polymer.

24. A process for preparing modified polysilacyclobutasilazanes comprising:
(A) simultaneously contacting and reacting in an inert, essentially anhydrous atmosphere, a polysilacyclobutasilazane polymer with dry ammonia and a mixture consisting essentially of 1,2-dichloro-1,1,2,2-tetramethyldisilane, 1,1,2-trichloro-1,2,2trimethyldisilane, and 1,1,2,2-tetrachloro-1,2-dimethyldisilane to form a modified polysilacyclobutasilazane polymer, and
(B) recovering modified polysilacyclobutasilazane polymer.

* * * * *